United States Patent
Koivumaa et al.

(10) Patent No.: US 11,464,449 B2
(45) Date of Patent: Oct. 11, 2022

(54) METHOD FOR MEASURING EXERCISE

(71) Applicant: Myontec Oy, Kuopio (FI)

(72) Inventors: Veikko Matti Koivumaa, Espoo (FI); Mikko Martikka, Vantaa (FI); Juha Kylliäinen, Siilinjärvi (FI); Arto Remes, Kuopio (FI); Pekka Tolvanen, Kuopio (FI)

(73) Assignee: MYONTEC OY, Kuopio (FI)

( * ) Notice: Subject to any disclaimer, the term of this patent is extended or adjusted under 35 U.S.C. 154(b) by 552 days.

(21) Appl. No.: 16/571,226

(22) Filed: Sep. 16, 2019

(65) Prior Publication Data
US 2020/0022651 A1 Jan. 23, 2020

Related U.S. Application Data

(63) Continuation of application No. 11/021,100, filed on Dec. 22, 2004, now abandoned.

(30) Foreign Application Priority Data

Dec. 22, 2003 (FI) .................................. 20031881

(51) Int. Cl.
*A61B 5/103* (2006.01)
*A61B 5/389* (2021.01)
*A61B 5/00* (2006.01)
(52) U.S. Cl.
CPC .......... *A61B 5/6804* (2013.01); *A61B 5/1038* (2013.01); *A61B 5/389* (2021.01)
(58) Field of Classification Search
CPC ...... A61B 5/6804; A61B 5/1038; A61B 5/389
See application file for complete search history.

(56) References Cited

U.S. PATENT DOCUMENTS

| | | | |
|---|---|---|---|
| 3,534,727 A | | 10/1970 | Roman |
| 3,610,250 A | * | 10/1971 | Sarbacher .......... A61N 1/36003 200/51 R |
| 3,835,840 A | | 9/1974 | Mount |
| 3,916,876 A | | 11/1975 | Freeman |
| 4,016,868 A | * | 4/1977 | Allison ................ A61B 5/6804 600/388 |
| 4,148,303 A | * | 4/1979 | Cohen .................... A61B 5/389 600/546 |
| 4,580,572 A | | 4/1986 | Granek et al. |
| 4,582,049 A | | 4/1986 | Ylvisaker |

(Continued)

FOREIGN PATENT DOCUMENTS

WO WO2004058346 A1 7/2004

OTHER PUBLICATIONS

Novacheck, T., "The biomechanics of running", Gait and Posture, vol. 7, 1998, pp. 77-95.

*Primary Examiner* — Rene T Towa
(74) *Attorney, Agent, or Firm* — Laine IP Oy

(57) ABSTRACT

The present invention relates to a method for measuring an exercise, in which method the electrical signals caused by active muscles are measured with a measuring device and response is given from the physical performance with a perceivable signal. In the method in accordance with the invention by measuring and analyzing EMG activities of muscles or EMG activities of muscles and movements of the body quantities describing the physical performance and/or the result of the physical performance are calculated or evaluated.

17 Claims, 5 Drawing Sheets

(56) References Cited

U.S. PATENT DOCUMENTS

Figure 1:
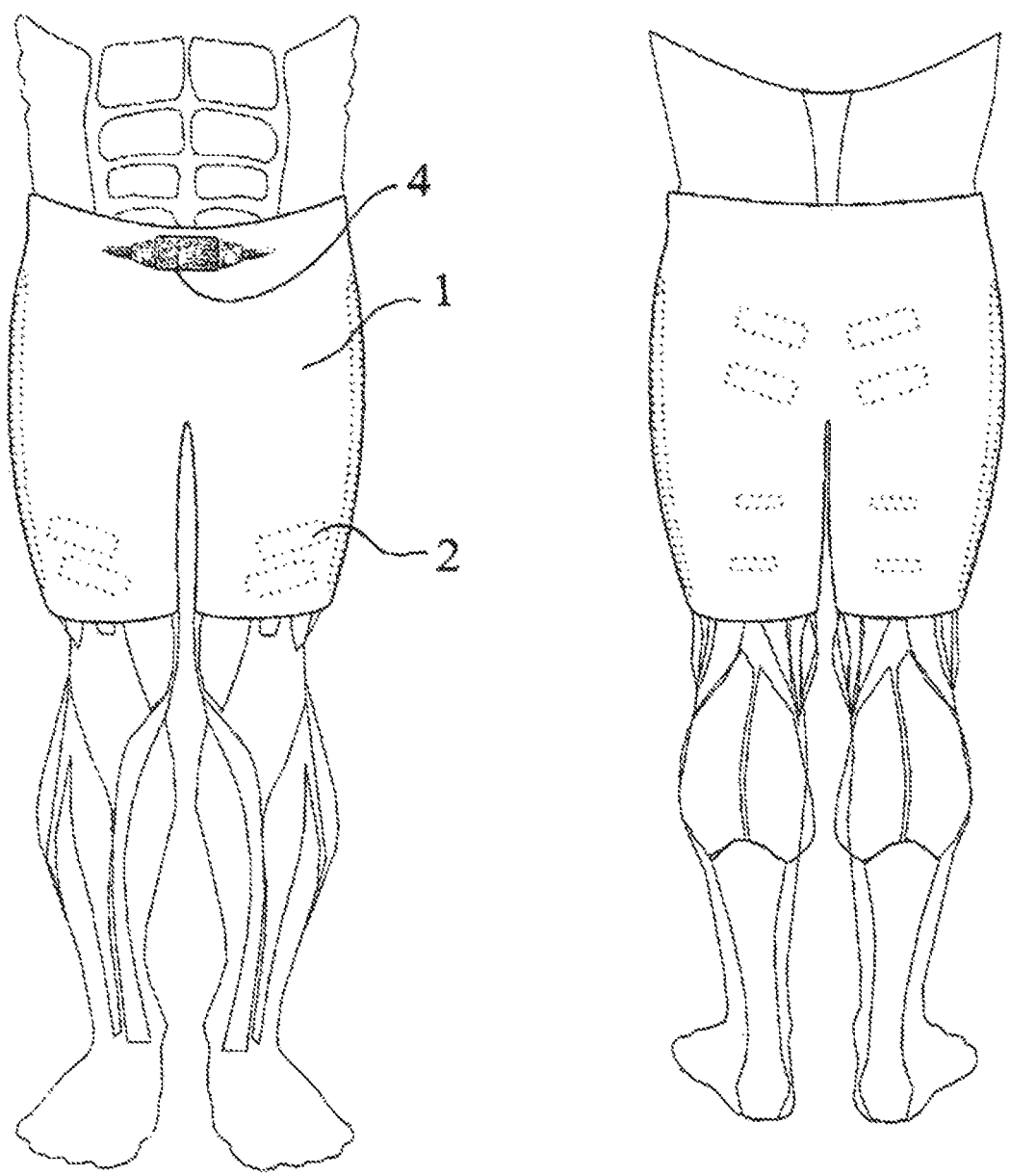

| | | | |
|---|---|---|---|
| 4,664,130 A | | 5/1987 | Gracovetsky |
| 4,729,377 A | | 3/1988 | Granek et al. |
| 5,368,042 A | | 11/1994 | O'Neal |
| 5,628,722 A | * | 5/1997 | Solomonow ......... A61F 5/0123 |
| | | | 602/26 |
| 5,740,813 A | | 4/1998 | Ogata et al. |
| 6,050,962 A | * | 4/2000 | Kramer .................. G06F 3/011 |
| | | | 600/595 |
| 6,129,666 A | | 10/2000 | DeLuca |
| 6,148,280 A | | 11/2000 | Kramer |
| 6,280,395 B1 | | 8/2001 | Appel et al. |
| 2002/0077689 A1 | | 6/2002 | Kirkland |
| 2002/0111557 A1 | | 8/2002 | Madill et al. |
| 2002/0165590 A1 | | 11/2002 | Crowe et al. |
| 2003/0135245 A1 | | 7/2003 | Campos |
| 2003/0139692 A1 | | 7/2003 | Barrey et al. |
| 2003/0229274 A1 | | 12/2003 | Standeven |
| 2004/0138583 A1 | * | 7/2004 | Galea ................... A61B 5/1107 |
| | | | 600/595 |
| 2004/0153007 A1 | * | 8/2004 | Harris .................. A61B 5/6807 |
| | | | 600/587 |
| 2005/0049517 A1 | * | 3/2005 | Mathew ................ A61B 5/389 |
| | | | 600/546 |
| 2007/0010761 A1 | | 1/2007 | Mo |

* cited by examiner

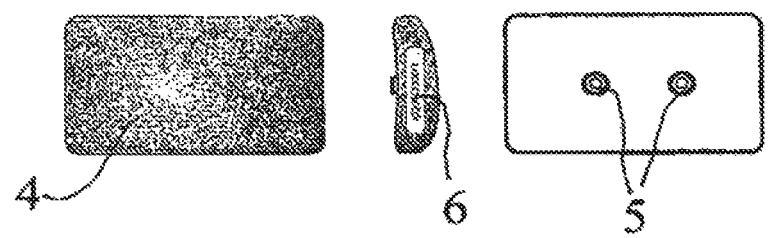
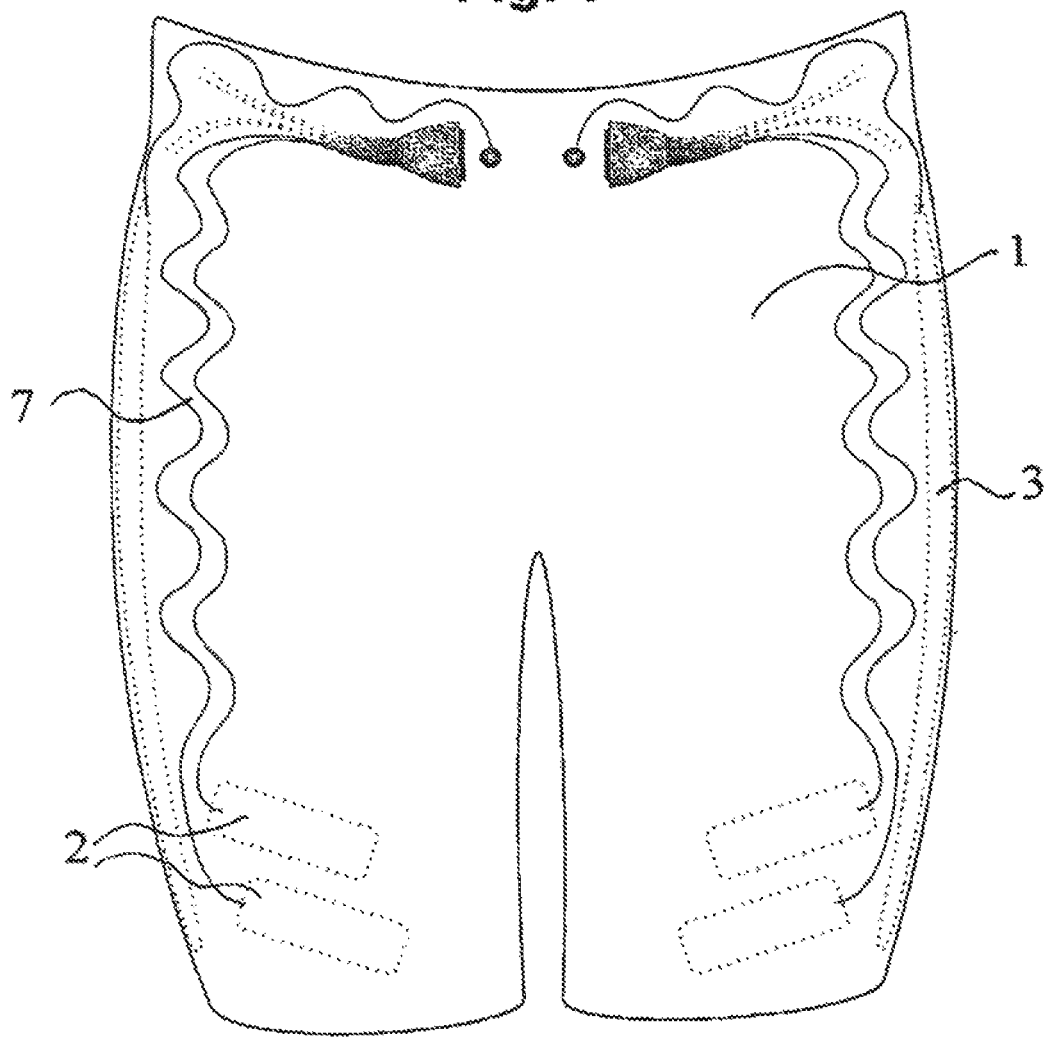

METHOD FOR MEASURING EXERCISE

The present invention relates to a method for measuring exercise by means of measuring the activity of muscles of the body, in which method the electrical signals caused by the active muscles are measured with a measuring device and response from the functioning of muscles and of the exercise is given to the user with a perceivable signal.

It is generally known that by means of EMG signal received from muscles it is possible to measure levels of activity of muscles and from those calculate various quantities describing the functioning of muscles and the body. EMG signals are usually measured through electrodes placed on the surface of the skin on muscles. Measured EMG signals are then typically transmitted either to be presented in real-time on a screen or signals are saved in a file format for later examination and analysis. Each EMG signal forms a so-called profile, in which the active and passive phases of the measured muscle are to be seen as variations of amplitude of a signal. In addition, the frequency spectrum of a signal includes information about the functioning of a muscle. Quantities describing the functioning of muscles are, among other things:

- muscle loading and variations in it
- distribution of loading on various muscles of the body
- a side difference of two symmetrical muscles, while loaded simultaneously or cyclically by turns
- activation order of muscles, activation times, reaction time etc.
- fatigue of muscles.

In addition, a great number of other quantities to be monitored and supervised may be calculated from the pattern, amplitude and frequency spectrum of an EMG signal and from variations in those.

It is common to monitor active muscle functioning and, at the same time, to give response of the functioning in different ways, such as in visual numbers, graphics or by means of sound. The response method is placed either in the measuring device itself or in a distance from it in a separate display unit. Many times these measuring and displaying units are, however, a part of a bigger system, in which case training and physical exercise must be performed in a specific space such as a sports laboratory or a gym.

With present methods, it is possible to gather information about training or physical exercise during training/moving but the problem is how to present the information and/or response immediately and the whole time in any performing place irrespective of the circumstances and/or the place. In addition, in many sports events real-time information about muscles of the body and/or limbs and their functioning is needed and with present equipment this kind of information may not be gathered.

Electrodes in measuring devices are usually round spot like electrodes with about 1 cm diameter. These electrodes are placed and attached usually on a muscle with some suitable attaching medium such as glue in the electrode itself, with a separate tape, belt etc. Electrodes are placed on the muscle to be measured, thus trying to attain as pure as possible EMG signal and, on the other hand, trying to avoid errors and disturbances from adjacent muscles. Therefore placing of electrodes must be carried out with extreme accuracy to ensure reliability, repeatability and comparability of measurements. In addition, electrodes may come off or remove from their place due to an exercise or perspiration.

Today so-called pedometers are commonly in use, with which it is possible to count steps during a physical performance. Knowing the number of steps, it is possible to count the walking and running rhythm and by means of the rhythm to assess the velocity of proceeding and the distance covered. In addition, while cycling it is possible to count, among other things, the number of revolutions of cranks in time unit, i.e. the cadence and the power output directed to pedals by means of similar equipment. With present pedometers, it is possible to count the number and the rhythm of steps for practical purposes reliably, but measurements of the velocity of proceeding and the distance covered are relatively rough estimations. In addition, the equipment in question has not the ability to adapt to outer factors such as variation of the terrain and the weather conditions as well as to individual or momentary changes in pacing.

With present pedometers, it is possible to count the number and the rhythm of steps and on that ground to assess the distance covered and the velocity used. The recognition of a pace is carried out by recognizing the mechanical movements in a pace by means of a sensor attached either to the body or to a running shoe. Estimation of the distance and the time is based either on the calculations carried out by means of an approximate pace length or, in more advanced models, on analyzing of the changes in the path of a foot seen as a function of velocity detected in the motion signal. The pace length is calibrated individually and it is fed as the initial data to the equipment. The weaknesses of these methods are the problems related to the measuring accuracy. The pace length and the shape of a pace of a runner vary, for example, because of the shape of the terrain, the degree of hardness of the ground, the amount of outfit, the direction of the wind etc. outer factors. In addition, along with the developing of the condition and the running technique the pace length may change either to be longer or shorter. In addition, by examining mere mechanical motions it is not always possible to recognize paces reliably, because the vibration generated in running may cause disturbances affecting the calculation of a motion signal.

To measure distance and velocity also equipment based on OPS locating are employed today. This equipment is, for the time being, rather expensive and, in addition, the power consumption requires a big and heavy accumulator or battery. Therefore, they adapt poorly to be used as a part of a small, multi-functional, portable device. GPS requires a clear connection from a device to a satellite and therefore measuring is not possible indoors and in the shades of terrain, for example, in a forest. Even short shades prevent continuous measuring and cause therefore errors in results. Due to the flying path of satellites, also the intensity of GPS signals varies in different parts of the earth and in different times of the day.

Today there are devices in use, in which a sensor placed in close proximity to the rotation path of pedal cranks in a bicycle frame counts the number of passings of a magnet placed in a pedal crank from which the number of revolutions of cranks in minute i.e. the cadence may be calculated. The problem with these meters is the mounting, which requires accuracy in defining the right distance between the magnet and the sensor, as well as the sensitivity for damages in mounting, for example, in mountain biking. In addition, employing this kind of cadence measuring in several bicycles requires mounting of a sensor and a magnet to each bicycle.

By measuring the velocity and the tightness of the chain of a bicycle as well as the number of revolutions of cranks, it is possible to assess the power directed to the pedal cranks and the distribution of power between legs. This kind of measuring indicates the power created by the body but no conclusion may be drawn from the result on what kind of muscle loading the measured power has been created i.e. what the efficiency of the physical performance is. For the same reason the use of the measuring of the created power does not enable the monitoring of cumulative total loading i.e. the amount of work. The use of measuring of power in several bicycles requires mounting of a sensor and a magnet in each bicycle as rapid mounting of sensing is not possible.

The available equipment for measuring of muscle loading is mainly meant for research use i.e. measurements may be carried out only in carefully selected times, in controlled circumstances and while guided by an experienced user. Apart from a measuring device also a separate computer and a programme are in most cases required, by means of which the measuring parameters interesting to the user are first defined to the device and, on the other hand, the results are available only afterwards analyzing the data gathered in the memory of the unit. The devices mentioned are not good enough for personal and every day use while they should be light, easy-to-use and economical.

Present measuring methods of body loading suitable for every day use are based on monitoring the heart rate and variations in it. When the loading is constant or changes in it are slow the heart rate is a good indicator of the loading level but in all physical performances, the monitoring of heart rate is not enough for estimating the optimal loading. During exertion, the heart reacts, in most cases, through changes in oxygen need to changes in the whole body, but it does not identify those parts of the body, in which the changes of loading are happening. In addition, the heart is not capable of identifying fast changes of loading, which, however, may affect the endurance, fatigue or the generating of substances causing stiffening, such as lactate, and therefore the performance itself. In addition, at least on low heart rate levels apart from physical loading also mental factors have influence on the heart rate. Outer factors, such as rises and falls in the terrain, contrary wind etc. and momentary changes in the running rhythm may cause unnecessary or premature fatigue of muscles of leg, which could be prevented by reacting quickly to the changing load. On the other hand, by monitoring only the heart rate the user is not, in all situations, capable of facilitating all power recourses in his or her body, in which case especially in competition may not reach the best possible performance level.

The training of endurance of muscles requires intentional loading of muscles with various power levels depending on which sector of endurance is desired to be developed. To raise basic endurance aerobic long-term exertion, carried out with light load, is required. On the other hand, so-called lactate exercises are meant to develop tolerance of extreme load and maximum loading levels are needed. In addition, depending on different sports various medium levels of earlier mentioned loads are needed.

With present methods, a loading is measured from one muscle at a time and thus a person's efficiency is tried to be assessed. An EMG measuring of one muscle describes the function of that muscle accurate but the results from that may not be generalized to describe the total exertion of that limb or part of the body in question. Therefore measurements must be carried out from different muscles affecting the motion of that limb and by summarizing the results from those the total loading may be assessed. In present equipment this means increasing of the number of measuring channels and thus more complicated and unpractical construction.

The purpose of the invention is to provide a method for measuring an exercise, with which the disadvantages of present measurings are eliminated. Especially, the purpose of the invention is to provide a method, with which it is possible to monitor and to assess an exercise and the quantities describing the results from it as well as to receive response from an exercise all the time immediately, reliably and simply. Further, the purpose of the invention is to provide a method, with which it is possible to get real-time information about the functioning of muscles and the level of efficiency during an exercise.

The object of the invention is accomplished by a method, the characteristics of which are presented in the claims.

In the method in accordance with the invention quantities describing an exercise and/or the result of an exercise are calculated or assessed by measuring and analyzing EMG activities of muscles or EMG activities of muscles and movements of the body. By means of a method in accordance with the invention, a user receives an immediate response about an exercise, functioning of muscles, balance of muscles and changes in balance etc., by means of which the user may regulate and improve the efficiency of an exercise and prevent weakening of efficiency due to fatigue of muscles.

In accordance with the invention the rhythm of an exercise and/or the total number of movements are advantageously measured such that from one or several EMG signals measured from one or several muscles during an exercise the number of activating times in it during a desired period of time is identified and by means of those the number of physical performances carried out in a time unit and/or the total number of physical performances are calculated. This means measurements of the rhythm of various sports events, repetitions of movements or the total number of movements. Monitoring of the rhythm of an exercise is important, for example, for exercising endurance, velocity and strength characteristics and for developing the economy of a performance. By means of the number of movements, for example, the duration and the total loading of a performance are monitored and, for example, the number of repetitions needed in the exercise is supervised. Endurance sports, such as running, cycling, skiing and rowing are often related with an optimal rhythm area from the proceeding velocity and energy consumption point of view, and following that rhythm area the best result is achieved. Developing of the condition of muscles, for example, by means of equipment at a gym or learning of a right performance technique require performance rhythms, number of repetitions and the total number of movements of very various levels depending on goals.

In an advantageous application of the invention, the rhythm of a physical exercise with alternating rhythm such as running or cycling is measured with one or several measuring devices. In the method in accordance with the invention, the activity profiles of EMG signals from muscles used in physical exercise are measured. During walking and running the pace rhythm and/or the total number of steps are counted from EMG signals during pacing from muscles of the front part and/or back part of the thigh and/or muscles below the knee i.e. by means of the number of contractions of muscles or muscle groups. Contractions in both legs are counted, in which case the number of steps may be identified from both legs separately and in that way secure the accuracy of the calculated rhythm. The equipment in accordance with the method may comprise also one or several motion sensors placed on the body and/or on the limb, in which case the accuracy of calculation may be improved even more by comparing results from various independent sources with each other. The number of steps is calculated by summarizing the number of identified paces in desired time period or during the whole exercise. The method in accordance with the invention offers a method more accurate and more adapting to changes than present pedometers to measure proceeding velocity and covered distance. In addition, the method may easily be applied also in other rhythmical physical performances requiring the use of legs, such as skiing, rowing, canoeing and in exercises at a gym.

In another advantageous application the calculation of the rhythm and the number of performances are applied in exercises requiring the same rhythm of the limbs. These kinds of performances are thrust and jumping exercises with both legs together. Another example is strokes of an oar during rowing, which include flexing of arms and simultaneous extending of legs on a sliding bench. In addition, calculation of the rhythm and the number of performances at a gym may be employed for guiding and monitoring the exercise programme.

In the next application of the invention with one or several measuring devices the proceeding velocity of walking and running are measured, which velocity is calculated by measuring the pace length by means of the time of the foot being on the ground and by multiplying the pace length by pace rhythm. From activity profiles of muscles the basic phases of a running pace, such as the take-off moment, the recovery phase as well as the striking moment and the toe-off moment may be identified in spite of the running velocity, style or individual differences. The shape of activity profiles and the activating moments of muscles vary, for example, due to running velocity and changes in the terrain. Especially, the time of the foot being on the ground in proportion to the whole pace is reduced while the walking or proceeding velocity increases. While walking one foot touches the ground the whole time but while running the both feet are in the air at the same time between paces. The time of a foot being on the ground may be identified and measured from activating phases of one or several EMG signals measured from one or several muscles. Therefore, the time of the foot being on the ground may be measured from the starting damping phase when the foot strikes the ground to the moment of activation of muscles creating the take-off. Gluteal muscles and the front muscles of the thigh are mainly responsible for the damping and the back muscles of the thigh provide the take-off. The recovery phase is assessed mainly based on the length of the resting time to be seen in the activity profile of the back part muscles of the thigh.

In an advantageous application of the invention the momentary proceeding velocity of walking or running is assessed by calculating the ratio of one and/or several loading levels during a pace calculated from EMG signal to the whole loading during a pace and/or the time of the foot being on the ground and/or the time used for a pace. For example, while the running velocity grows the loading of the muscles of the front part of the thigh increases more than the total loading of muscles of the back part of the thigh, in which case the ratio of the loadings is proportional to the running velocity. This ratio may be changed by means of a suitable calibration method to give the running velocity.

A calculation method for proceeding velocity is based on a formula: the pace rhythm*the pace length. The pace rhythm is calculated as earlier presented. In running the definition of the pace length is based on the fact that the time of the foot being on the ground correlates with the pace length, that is, kinetic resistances are also seen in it. The time of the foot being on the ground is measured, for example, from the acceleration and EMG signals such that the starting point is the activation of the front thigh muscle while the foot is hitting the ground, found out from so-called Averaged EMG (AEMG) and the finishing point is the minimum of vertical acceleration found out from the inertia signal after the activation moment and before the next activation of the front thigh muscle. This calculation may be carried out on both legs separately during running, in which case the accuracy of calculation increases.

Individual calibration of proceeding velocity is carried out separately for walking and running velocity. The length of a running pace is calibrated by measuring the time of duration of the foot being on the ground t and the number of steps used for that distance using two or several velocities. The distance for a run may be, for example, 100 m flat country. In running the pace rhythm r is calculated as a number of peaks found from inertia and/or EMG profiles in a time unit. Based on times of the foot being on the ground t measured with different velocities the pace length function $l=l(t)$ is defined. The running velocity is given by formula:

$$v = r * l(t)$$

In walking the pace rhythm is measured with two different velocities and at the same time the time used to the both performances, from which the velocity function $v=v(r)$ is defined. The walking velocity is given by formula:

$$v = v(r)$$

From inertia signals it is possible to define whether walking or running is in question. While standing still the vertical acceleration=the gravity of the earth i.e. 1 G. During running when the both legs are in the air the centre of gravity is part of the time in free fall and then the vertical acceleration=0 G. When walking the absolute value of the vertical acceleration is always >0. Limit may be defined to this acceleration, which is interpreted as a threshold state of walking and running styles. By identifying the moment of free fall or the vertical acceleration being below sufficient small limit it is possible to identify a motion to be running. For example, according to the rules of a competition walking at least one foot must touch the ground all the time. By mounting a device applying the method to the body of a competitor, it is possible to continuously control the purity of a performance.

A proceeding style may also be identified by the ratio of the pace rhythm to the time of the foot being on the ground. When walking the ratio of the time of the foot being on the ground to the pace rhythm is clearly smaller than when running. Either solid limits are given to the ratio or they may be calibrated individually. For example, if the ratio is smaller than the comparison value A then walking is in question and if the ratio is bigger than B proceeding is running.

Quantities obtained from one or several EMG signal measured simultaneously proportional to the proceeding velocity may be employed as comparison information, by means of which the calculation accuracy of velocity calculation is improved. For example, while the running velocity grows the summarized total activity of leg muscles grows, but the growth is not divided evenly among all muscles. The importance of the front part of the thigh is emphasized, which appears as growth of the total activity level of muscles in that part relatively more than what happens in the back part of the thigh. This ratio is facilitated while calculating the running velocity. As the time of the foot being on the ground gets shorter while the proceeding velocity grows one gets proportional variables to proceeding velocity from, for example, ratio of the activity level of the front thigh to the time of the foot being on the ground as well as from the ratio of the activity level of the front thigh to the time spent to a pace.

The summarized total activity of muscles used while running grows as the proceeding velocity grows, but the growth of activity is not linear. The amount of the total activity depends on how well the work of muscles changes in the body into biomechanical motion. When walking the total loading is relatively bigger than when running at the same speed. When starting running the ratio of the total loading to the running speed first decreases until it reaches the level where biomechanical motions and then paces are the most economical. Typically, the ratio of loading to velocity is at smallest on the speed area of 10 km/h . . . 20 km/h. When the speed grows from here further the muscle loading starts to grow relatively faster than the speed, until the situation is reached where the speed does not grow although muscles are loaded to maximum. The value of summarized total activity of muscles is facilitated when the proceeding velocity is assessed.

In activity profiles, also other characteristics changing as functions of velocity, shape of terrain, wind or other outer influences may be found. When proceeding at even velocity the loading of the body as a whole grows when going uphill and decreases in downhill but on the muscle level, the changes in the loading are divided in another way, for example, for holding the balance and due to a suitable style for the shape of terrain or for going against the wind. For example, when running uphill or downhill the mutual loading relation and timing of muscles of the front part and of the back part of the thigh change, because muscle strength is needed to driving forward in the rising phase but when coming down more muscle strength is used also for braking. When running uphill the activity level of the peroneal muscles raises but the activity level of the tibial muscles gets lower. Thus the mutual loading relations of muscles are facilitated while estimating the proceeding velocity.

One or more inertial sensors placed on the body are employed to measure movements of body and limbs, which sensors are, for example, acceleration sensors, angular acceleration sensors, angular velocity sensors i.e. gyroscopes or some other sensors or methods, with which movements of the body and/or limbs may be detected. Using information from signals simultaneously measured from one or more inertial sensors placed on the body the accuracy of calculation is improved. For example, the pace rhythm may be identified apart from a vertical acceleration signal also from an acceleration signal sideways.

Among inertial sensors, acceleration sensors are used as an example. Acceleration sensors give a signal proportional to acceleration of the movement in defined direction. In devices, one, two or three directions may be facilitated. The most natural place for acceleration sensors is the middle part of the body, however, equivalent information may be distinguished in case sensors are placed on other parts of the body. In up/down direction it is possible to calculate the number of steps and the pace rhythm most easily.

In an advantageous application of the method the time of durations of a foot being on the ground is measured such that simultaneously with measuring the EMG signal also one or two inertia signals are measured and from those the time on the ground is identified and measured. In another application the moment of the foot striking the ground is identified from the activation moment of the front thigh and the coming off from the ground of the foot from the minimum moment of vertical acceleration signal. In sideways direction, the rocking sideways of the body may be noticed and the sensor of proceeding direction tells about acceleration variations related to proceeding.

The accuracy of calculation is improved by using the information from simultaneously measured signals from one or more sensors placed on the body and monitoring the shape and changes in terrain as comparison information. For example, air pressure sensor placed on the body gives an air pressure signal, which varies in accordance with difference in altitude of terrain. Fast variations of shape and the steepness of uphill/downhill angles in terrain are identified with an inclination sensor. By analyzing these signals it is then concluded whether one is moving on even land or uphill or downhill and the direction and the magnitude of changes is found out, which information is then employed for specifying the calculation of the proceeding speed. For example, loading variations in EMG signals caused by the changes in terrain may be taken into account as specifying factors of the results.

Devices applying the method in accordance with the invention include the possibility to specify the measuring of the proceeding speed also with factors depending on individual differences. Individual constant factors related to earlier described variables such as the weight of the runner and the length of the leg are fed as initial data to the measuring device. These data correct the results of the proceeding speed based on the database. Calculation of proceeding speed may also be carried out by making an individual calibration, which is made by walking and/or running a known distance, measuring the time covered and feeding this information to a measuring device, which calculates an individual variable table for velocity measurements.

Calculation of proceeding speed may also be carried out with the method in accordance with the invention by facilitating an individual pace length. In introduction of the device an individual pace length may be defined either in a traditional way by measuring the pace length or by doing a calibrating run or walk of known distance, from which the number of steps or the time used is calculated. The pace length is fed to the measuring device, which facilitates it in the future while calculating running speed and distance.

The distance covered during walking or running is calculated by summarizing the lengths of measured paces. Other methods of measuring are, among others, the product of the number of steps and the average pace length or the product of the average speed and the time covered.

With calibration, also EMG and acceleration profiles proportional to the run are registered. The initial value of the pace length may be updated during the run by comparing the changes of EMG and acceleration profiles with each other. For example, while running on a flat country against the wind with the same EMG activities the pace gets shorter or the pace of the same length requires greater EMG activities. The change in the pace length may be identified from the acceleration profile and correspondingly the extra loading used to a normal pace length from EMG profiles. When outer changes are noticed to affect the pace length the calibrated pace length is changed momentary by means of those and such also the calculations on speed and distance are defined more closely.

In the next advantageous application of the invention while riding a bicycle by means of the method in accordance with the invention the number of revolutions of cranks in time unit and/or the total number of revolutions of cranks may be defined by calculating the number of contractions of muscles from EMG signals from muscles having influence on rotating the pedal cranks, for example, muscles or muscle groups of the front part of the thigh and/or the back part of the thigh and/or muscles or muscle groups under the knee per time unit. The calculation of contractions is carried out for both legs, in which case the number of revolutions may be identified separately for both legs and such increase the accuracy of the calculated number of revolutions of cranks in time unit. While the method in accordance with the invention is based on trunks worn by a cyclist and on a measuring device attached to those trunks, the use of the method is easy and advantageous irrespective of the number of bicycles in use.

In the next application of the invention the loading on the body is measured in real-time during an exercise and on the base of the measurement the loading level on the body, limbs and/or muscles, as well as the distribution of the loading on various parts of the body and the cumulatively gathered loading and/or the work carried out and their corresponding distributions are assessed. The loading on the body is measured in recognized, so-called Averaged EMG calculation (AEMG), which is based on the interpretation of bi-polar EMG signals measuring the activity of muscles. The signals are rectified and averaged over suitably chosen time period, in which case the quantity describing the current loading is obtained. When the averaging is carried out as sliding calculation the measuring results will be available in real-time and immediate response may be given to a user. The averaging time is chosen depending on typical rhythming of an exercise and biomechanical factors such that the results from calculations describe as well as possible the real effective loading during changes, among other things, in terrain, proceeding speed or circumstances. In addition, other averaging criteria are defined such that the AEMG calculation reacts quickly enough to the meaningful changes in muscles, but the measuring result is, however, stable enough to keep in form understandable to a user. Short, momentary changes in EMG signal and possible disturbances may not misrepresent the effective value of the loading.

With the method in accordance with the invention the momentary loading level of legs is measured by averaging the AEMG levels measured from chosen most important muscles or muscle groups of both legs and summarizing those, in which case the momentary loading level describing the total loading of legs is obtained. The result of the calculation is typically given as numerical value, the unit of which is $\mu V$. The cumulative total loading from a certain time period is the cumulative integrated AEMG sum i.e. the calculatory square area formed by EMG data and time. The result is typically given as numerical value, the unit of which is $\mu Vs$.

In accordance with an advantageous application of the invention, the momentary total loading of a performance is measured by summarizing momentary AEMG values gathered from all measured muscles and comparing the result with the reference value.

In the next application, the cumulative total loading of a performance is measured by summarizing cumulative AEMG values from all measured muscles and comparing the result with the reference value.

The measuring result is given in earlier mentioned applications as proportioned to, for example, a reference value relating to a person, performance or sports, which value makes possible different loading comparisons. Among others, so-called Maximum Voluntary Contraction value (MVC) is used as a personal reference value, which is carried out by doing a muscle-by-muscle maximum loading test, which describes the maximum performance capacity of the muscle in question. Other reference values may be, for example, some other standardized test result such as, for example, a run in constant speed of 400 m lap etc. load test related to a sports event. The basis of a reference value may also be the ratio of two changing values, for example, momentary muscle loading during a run divided by momentary running speed. The ratio of loading and speed functions, in that case, as an economy indicator while exercising a less loading running technique. Both the momentary and the cumulative result may also be illustrated in other ways, for example, as a graphical or some other visual view or as a voice response.

Measuring and comparing of differences between functions of symmetric muscles in various sides of the body and limbs during different kinds of physical performances is one application in accordance with the invention. Quantities to be measured are, for example, the side difference between loadings of the limbs located on left and on the right side of the body, the ratio of loadings of the upper part and the lower part of the body or corresponding distributions measured based on some other division. In this case, the muscles of the weaker side or body part may be developed for improving sport performance, for preventing stress injuries or restoring normal efficiency after an injury. The result may be presented as quantities describing both momentary and cumulative loading ratio and they are given typically as numeric %-values.

In an application of the invention a momentary loading of the left and/or right side is measured by summarizing momentary AEMG values measured from all left side muscles and/or right side muscles and by calculating the ratio of momentary loadings of left and/or right side to simultaneous momentary total loading.

In the second application of the invention the cumulative loading of left and/or right side of the body is measured by summarizing the cumulative AEMG values measured from all left side muscles and/or right side muscles and by calculating the ratio of loadings of the left and the right side to simultaneous cumulative total loading.

In the next application of the invention the momentary loading of the upper part of the body and/or lower part of the body is measured by summarizing the momentary AEMG values measured from all muscles of the upper body and/or muscles of the lower body and by calculating the ratio of momentary loadings of the upper and/or lower part to simultaneous momentary total loading.

In the next application of the invention the cumulative loading of the upper part of the body and/or lower part of the body is measured by summarizing the cumulative AEMG values measured from all muscles of the upper part of the body and/or lower part of the body and by calculating the ratio of cumulative loadings of the upper part and/or the lower part to simultaneous cumulative total loading.

In the next advantageous additional application of the invention the function of so-called action—reaction muscles i.e. agonist/antagonist muscles is measured and the relation of their muscle loadings in various situations are calculated. Typically, the question is of measuring the loadings of muscles of the same limb affecting movements directed to opposite direction. The ratio of loadings depends on what kind of physical performance is in question. For example, in skiing and in Nordic walking with sticks greater work is done with the extensor of brachium than with the biceps; in rowing, on the other hand, the other way round etc. In this case, it is possible to develop the co-operation of muscles affecting movements of a limb or a joint related to sports event in order to achieve the maximum use of power and/or as good as possible performance endurance. For example, during running the muscles of the back part of the thigh have much greater meaning to the performance endurance than the muscles of the front part, especially when the running speed is increasing. The muscles of the back part of the thigh of an inexperienced runner get tired faster than the muscles of the front part. By monitoring the loading ratio of muscle groups of the front and the back part of the thigh, it is possible to estimate the development of the running condition of a person. The optimal loading ratio is measured similar to the side differences. The result may be presented as quantities describing both momentary and cumulative loading ratio and they are given typically as numeric %-values.

The method in accordance with the invention may be applied both for monitoring the optimal performance level during the exercise and during an exercise phase for keeping up the appropriate high loading levels.

While employing the method in accordance with the invention disturbances due to physical performance to EMG measuring signals are minimized by employing filtering methods suitable for filtering, with which such frequency bands are dampened and/or eliminated from EMG signal, where movement disturbances or other disturbances related typically to the performance and/or measuring method distort the EMG signal. The typical EMG frequency band of muscles is about 10 Hz-500 Hz, which is generally employed in scientific research or while carrying out diagnostic EMG measurements. In research situations, movement disturbances are prevented, among other things, by removing hair and grinding the surface of the skin at points of electrodes as clean as possible as well as using conductive gel between electrodes and the skin. In addition, the attachment of electrodes and leads from those is secured, for example, by taping them on the skin. In this way measuring results are scientific accurate, but the method is not suitable for regular practical measurements, for example, for monitoring daily training. The abrasion of electrode surfaces against the skin due to rhythmic movements of legs during running generates disturbances on the band typically about 1 Hz-40 Hz, which distort the amplitude of the EMG signal to be measured on the band in question. In other forms of physical exercise there are similar disturbance factors, but the frequency bands are not necessarily the same. In case a device in accordance with the invention, which has specially been meant for monitoring running, includes filtering eliminating disturbances in question, the device gives a sufficient accurate measuring result in terms of the loading of running. Although the accuracy of the measuring result does not meet the criteria employed in scientific research the measuring results gathered from EMG signals filtered in accordance with the method are comparable among themselves and well suitable for monitoring the variation of loading.

The method and the outfit may be used for various purposes. Generally speaking, the method and the device are suitable for monitoring sports performances and for improving efficiency. Typical objects for the method is the use of the main muscle groups (the thighs, the calf and the lower leg, upper arms, abdomen, back etc.) in various sports events, such as cycling, running, skiing, jumping events, power training, weight lifting etc. in which using various levels of muscle load the training is in each case directed to desired purpose. Basic endurance is developed with low loadings whereas speed and power endurance with great loading levels. In addition, devices in accordance with the invention may be employed for rehabilitation of side difference of muscles due to being injured or for learning the right motion path of a limb by means of muscle strengths of right magnitude.

In various sports events muscles needed in those or related to those are stressed by training. By means of the method in accordance with the invention, various muscle groups and/or various functions are monitored depending on the sports event. Next, as examples, various sports events are presented but the method and the outfit in accordance with the invention may naturally be applied also in other events.

In running, also the optimal relation of running speed and muscle loading, the total loading level suitable for changes in the terrain as well as the balance between the left and the right leg are tried to be taken care of. Measurements are carried out as averaged over regulable time or during chosen number of pacing. In addition, the right relation of the extensor and the flexor of the knee is monitored in order to find a low, efficient running step of right length.

In cycling, evenly controlled number of revolutions of cranks in time unit, which is suitable in terms of gear transmission, the balance of the left and the right leg as well as the total loading of the thighs are tried to be taken care of. Measurements are carried out as averaged over regulable time or during chosen number of crank revolutions. In addition, the optimal relation of the extensor and the flexor muscles of the knee is monitored, the objective being to "rotating" the pedals, instead of "treadling", in which case more even power transmission is gained from pedals to the chain and, on the other hand, the fatigue of muscles of the front side of the thighs is prevented.

In cross-country skiing, the method may be utilized in optimizing the muscle endurance on distances of various lengths and/or in various terrains. In Alpine skiing events, correspondingly, by means of the method the maximum power supply needed in extreme situations, but, on the other hand, also the right relaxing of muscles during the performance for preventing unnecessary fatigue may be developed.

In training in gymnastics and at a gym, as well as in muscle training the number of physical performances, the total loading of muscles of chosen left and right side, the balance between them, as well as the optimal relation of chosen extensors and flexors are monitored. In addition, also other muscle groups are monitored, such as abdomen/back muscles, with which the posture and the balance are maintained.

In jumping events the total loading in two feet take-off, synchronization, activating and reaction times, the balance between legs (thighs, calves etc.) and while taking off by one foot the co-operation of muscle pairs affecting the extending and flexion of the knee and the lower leg are monitored. In throwing events, the relations of work done by extensors/flexors of legs and arms and/or muscles of the back/abdomen affecting the turning of the body are compared.

Various exercises and measurements are related with ball games. By measuring muscle loading, the loading of physical performances typical to this event and especially the changes of the loading during a game may be assessed. In football, the difference between muscle activities of kicks on the left and the right leg and the measuring of kicking technique are important. In addition, by means of the method it is possible to compare the efficiency of turns to the left and to the right as well as the technique of performance, for example, in ice hockey.

Figure 4:
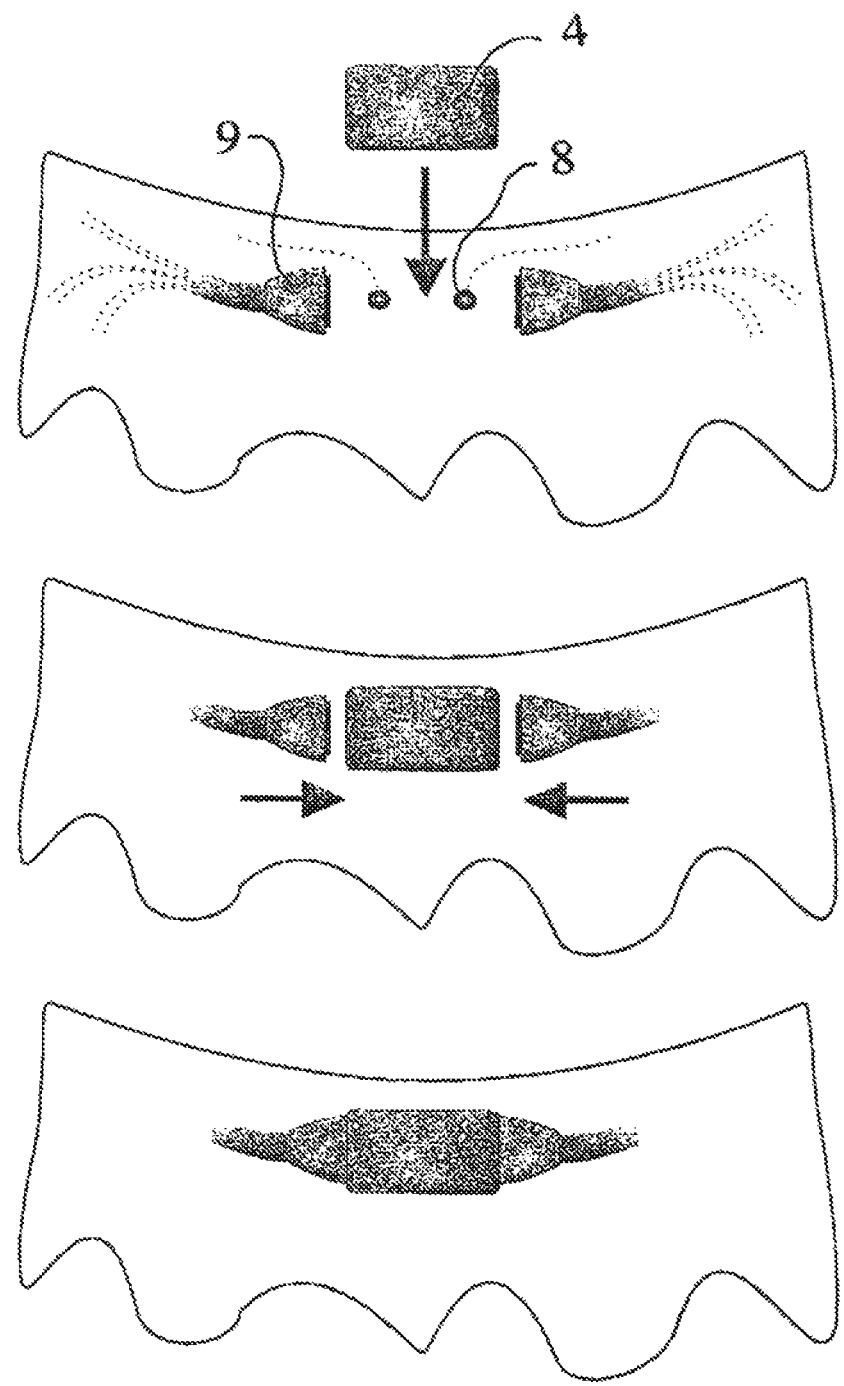
Figure 5:
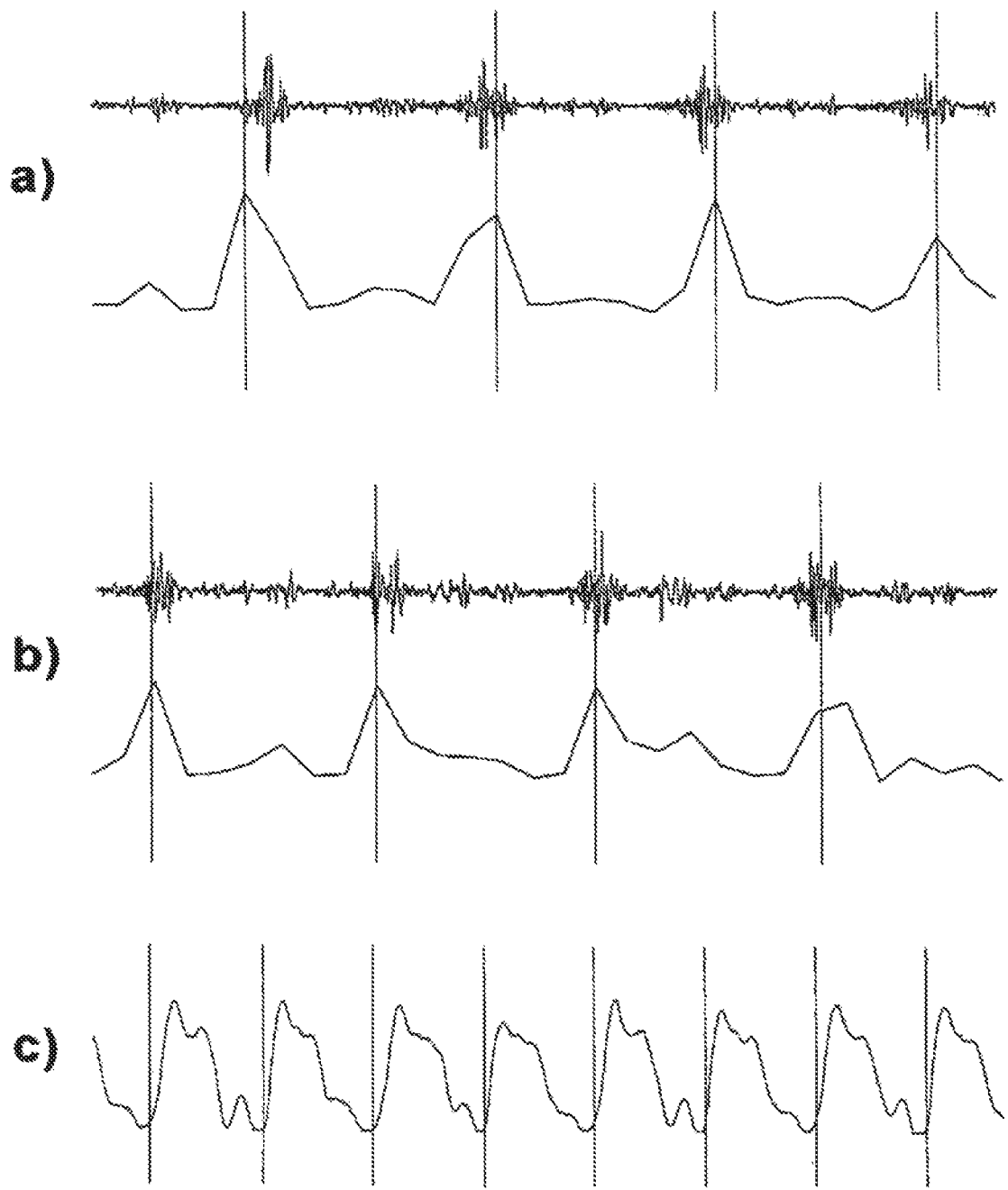
Figure 6:
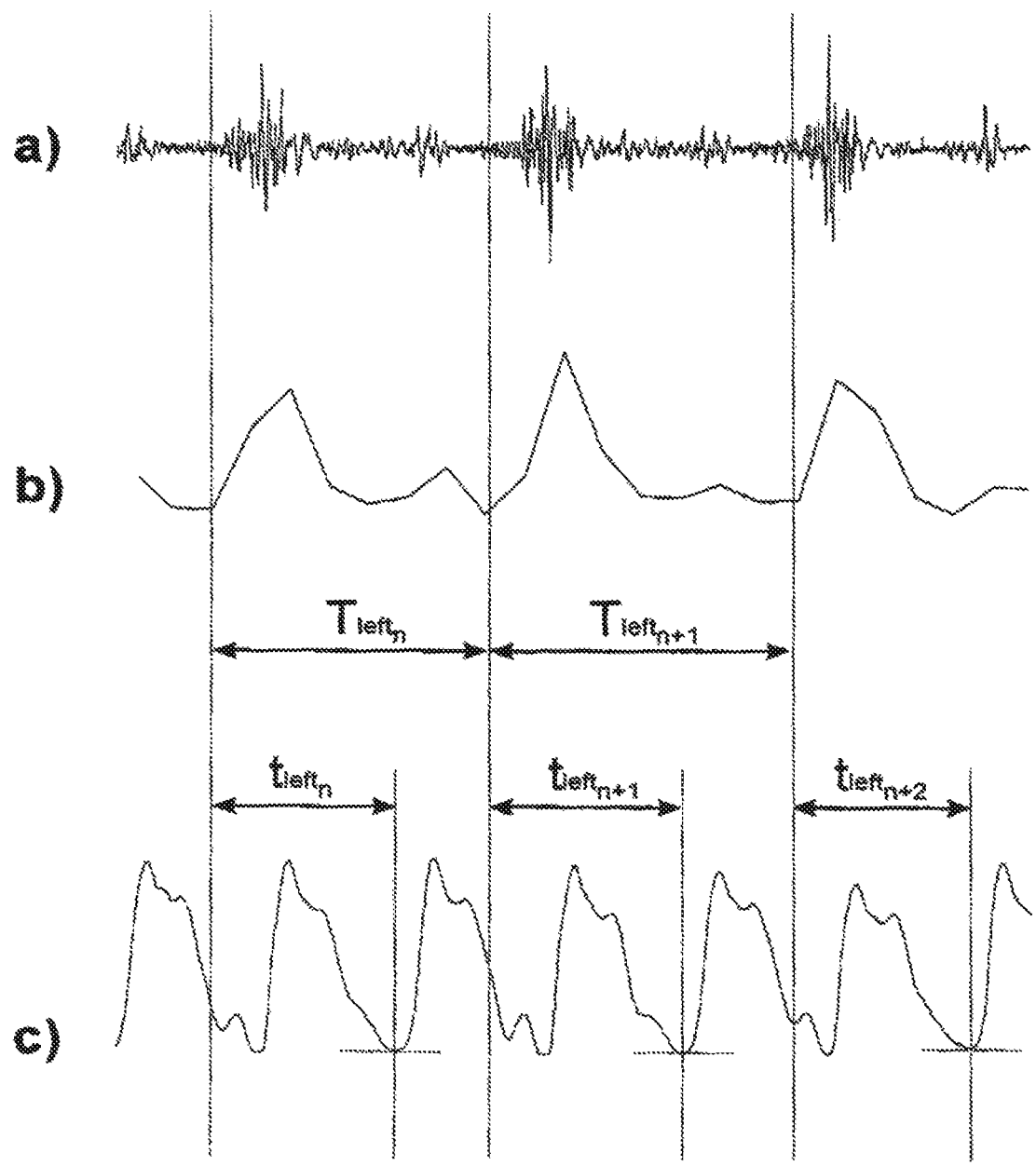

Next, the invention will be explained in more detail with reference to the accompanying drawings, in which, FIG. 1 illustrates the outfit with the measuring equipment in accordance with the invention viewed from ahead and from back, FIG. 2 illustrates the measuring module from ahead, side and from back FIG. 3 illustrates the placement of electrodes, conductors and connectors in trunks, FIG. 4 illustrates the attachment and connection of the measuring module to the trunks, FIG. 5 illustrates the identifying of walking/running rhythm from EMG and inertia signals, FIG. 6 illustrates the identifying the time of the foot being on the ground from EMG and inertia signals.

FIG. 1 illustrates the outfit 1, trunks with electrodes 2 placed to desired points as well as the measuring module 4 attached to its place. As electrodes recognized textile electrodes suitable for the purpose are used but also other kinds of electrodes may be used in other applications. These electrodes have been connected to the measuring module attached to the trunks illustrated in the figure. The signals from the electrodes to the device are connected with conductive fibres attached to the trunks or by using some other recognized conductor.

In addition, the system comprises a response device, to which the desired data from the module may be transmitted either along a wire or wirelessly in a recognized way. The response device is not illustrated in the figure. The response device may be attached to the body of the user, for example, to the wrist or it may be placed on the same outfit, it may be on a different outfit or in some device, which the user carries with him or her self. The device may also be located in the means, in which the user is or with which he or she is moving and/or the desired information may be transmitted to one or several other devices at a distance in a recognized way wirelessly.

In the method in accordance with the invention muscle activity is measured from electrodes placed on muscles to be measured and integrated to an outfit, for example, to trunks, from which electrodes a signal is conducted to a measuring module for analyzing by means of a signal processing electronics and a programme. While the electrodes and the leads are attached to the outfit there is no need for separate electrodes and leads to be glued on the skin. Due to outfits of right size and their elastic fabric, the electrodes stay during the whole exercise time on their right place keeping up a reliable contact between the electrodes and the skin. Also a separate wearable sensor may be employed for measuring muscle activity, which sensor has the needed electrodes integrated to it. This kind of sensor may be placed to a measuring point either by attaching the sensor to an outfit covering the point in question or the sensor may be attached on the muscle by means of an elastic band, belt etc. suitable means. A sensor i.e. an electrode and leads refer, in this case, to any method or material, with which the electrical signal from a muscle may be measured and lead to a measuring module.

While wearing the outfit the electrodes are not placed exactly on a specific muscle, which is not even necessary while wearing an outfit in accordance with the invention, as the main objective is to compare the total work of limbs and not the work of an individual muscle.

There are textile electrodes, a data processing module, conductors made of conductive textile and one or more response modules advantageously integrated to the outfit. Recognized suitable for the purpose electrodes and conductors are employed as textile electrodes and textile conductors. Also other kinds of electrodes may be employed in other applications. The electrodes, conductors and connections are washable and wear-proof.

There are connections on the outfit, to which the module may removably be placed, and in the outfit and in the module there are connection parts equivalent to each other. There are standardized connection surfaces in the outfit and in the module, in which case the same module may be employed in several outfits. As an outfit wears out and the parts may be changed to another outfit this enables the use of the same modules for a long time, which reduces costs. There are one or several uniform grounding electrode surfaces in the outfit, which are employed as reference surfaces for measuring electrodes. A uniform grounding surface reduces the number of grounding leads needed in the outfit and, on the other hand, takes the grounding point as close as possible to the muscle/muscle group to be measured. A large grounding electrode surface secures the good contact also while moving. Grounding connection may also act as a disturbance protection for leads from measuring electrodes while needed.

A measuring module 4 has been presented in more detail in FIG. 2. In the bottom of the module, the counter parts 5 of press-studs and the multipole connectors 6 may be seen. Those are compatible with the connectors in the trunks. The measuring device may, while desired, be taken off, for example, for washing time or while removed to another outfit equipped with equivalent connection.

FIG. 3 illustrates as an example a way of the placement of electrodes, conductors and the measuring module in trunks 1. The measuring sensory has been integrated to the trunks, which sensory comprises measuring electrodes 2, reference that is grounding electrodes 3, presented with dashed lines, conductors 7 from electrodes to the measuring device as well as the connections for attaching the conductors to the measuring module. The electrodes 2 are placed, in this case, at the thigh on the trunk leg and the measuring point, viewed from the front, somewhat above the knee. The electrodes in the figure are electrodes measuring the EMG signal from the muscle group of the front thigh. On the backside of the trunks there are also electrodes similarly placed for measuring muscle groups of the back thigh and gluteals. There are two pairs of electrodes in the front part of the trunks and four pair in the back part. The pairs are placed symmetrically among each other. The electrodes have been connected for transmitting the data to the measuring module by conductors 7, which have been attached to the trunks wavelike for securing the sufficient elasticity of the outfit. The grounding electrodes, which may be seen on the sides of the trunks, are common to all measuring electrodes on the same leg. Electrodes are so-called textile electrodes and the conductors are made of conductive textile material.

FIG. 4 illustrates in more detail the connection of the trunks and the measuring module in the front part of the trunks. On the waist of the trunks, there is a connection area, with press-stud connections 8 and multipole connectors 9. On the backside of the measuring module 4, there are the counter parts 5 for the press-studs presented in FIG. 2, through which counter parts the module both simultaneously is attached mechanically to the trunks and the grounding electrodes are connected electrically to the module. On the sides of the measuring module, there are the counter parts of the multipole connectors, which are needed in connection of the measuring electrodes electrically to the measuring module.

In the FIG. 5 the measuring of pace rhythm from the thigh muscles of leg and by means of an acceleration sensor placed at the waist on the body are illustrated. The upper curve in FIG. 5 a) illustrates so-called raw EMG signal measured from front thigh muscles of the left leg and the lower curve the same signal while rectified and averaged (AEMG). In FIG. 5 c) there are equivalent signals from the tight muscles of the right leg. The curve of FIG. 5 c) is a signal from an acceleration sensor, which has been measured from a measuring module placed on the waist. In both thigh muscle signals pulses caused by the activation of muscles during pace and alternating in the rhythm of pacing, may be noticed. The pulses may be identified by the programme both from raw and AEMG signals. The momentary pace rhythm may be obtained, for example, by summarizing the pulses found out from the both legs during suitably chosen sliding time window. The total number of steps during a certain time period is the total sum of all pulses. In the acceleration signal rises and falls of the body caused by both legs are seen. By comparing the results from all three signal sources, the calculation of pace rhythm and the number of steps will be more accurate than with equivalent methods.

FIG. 6 illustrates the calculation of the time of the foot being on the ground for calculating the proceeding speed. As an example the time of the foot being on the ground is measured from the EMG signal of the muscle group of the left front thigh and by means of the signals from the acceleration sensor measured from the vertical acceleration placed at the waist in the body. At the point a) there is so-called raw EMG signal from the muscle group of the left thigh and at the point b) the same signal as rectified and averaged (AEMG). At the point c) there is the vertical acceleration signal, in which the accelerations noticed in the body due to steps of the left and the right foot are seen. When a foot strikes the ground, the front thigh muscles activate to receive the forces directed to the body. When the foot comes off from the ground in the take-off phase, the situation is seen as a change in the direction of the acceleration signal. The time between the rising edge seen in the AEMG signal and the minimum of the acceleration signal following it is defined as the time of the left foot being on the ground $t_{left_n}$. The points of the signals in question have been chosen because they are the easiest to be identified by the programme, but the time on the ground may also be calculated from other changes seen in the signals. The whole pacing time of the left foot $T_{left_n}$ is also marked in the figure.

The structure of the outfit may also vary in different applications of the invention. In different sports events different kinds of outfits are used, such that the structure, shape and the placement of the electrodes depend on the sports and the training event and on the fact what muscle groups are desired to be observed and monitored. For example, trousers and a long sleeve blouse are typical measuring outfits apart from trunks illustrated in the figures, with which it is possible to measure several sports events and physical exercises stressing the entire body.

The invention is not limited to the presented advantageous application but it can vary within the frames of the idea of the invention formed in the claims.

The invention claimed is:

1. A method for monitoring exercise performance in an individual comprising:
   measuring electromyogram (EMG) signals from one or more active muscles during an exercise by an individual via a plurality of electrodes and at least one grounding electrode, wherein the plurality of electrodes comprise at least one electrode on each of opposite symmetrical limbs of the individual, and wherein the plurality of electrodes and at least one grounding electrode are associated with an outfit during the exercise;
   measuring movement of the individual during the exercise via one or more sensors associated with the individual;
   determining, with a first computing device, results of the exercise from both the measured EMG signals and the measured movement, and
   transmitting the results from the first computing device to at least a second device;
   wherein the determining results of the exercise comprises determining at least one of a number of revolutions of cranks in time unit in cycling or a total number of crank revolutions in cycling,
   wherein the number of revolutions per unit of time and the total number of cranks revolutions are determined from EMG signals measured from at least one of: muscles on a front part of a thigh, muscles on a back part of the thigh, or muscles below a knee of the individual during cycling.

2. The method of claim 1, wherein the results further comprise one or more of: a total number of movements of the opposite symmetrical limbs; a rhythm of movements of the opposite symmetrical limbs; or a loading level of the opposite symmetrical limbs.

3. The method of claim 1, wherein the determining results further comprises:
   determining a loading level for each of the opposite symmetrical limbs; and
   determining a ratio of loading levels from the loading levels of the opposite symmetrical limbs.

4. The method of claim 1, wherein the at least one measuring electrode for each opposite symmetrical limb comprises a first measuring electrode sized and shaped to extend across a front thigh of the individual and a second measuring electrode sized and shaped to extend across a back of a thigh of the individual, and the measuring comprising simultaneously measuring EMG signals from the front and back of the thigh of the individual.

5. The method of claim 4, further comprising determining a loading level ratio for the front and back of the thigh from the simultaneously measured EMG signals from the front and back of the thigh of the individual.

6. The method of claim 1, wherein the results of the exercise further comprise a comparison between a total amount work of the opposite symmetrical limbs rather than work of individual muscles.

7. The method of claim 1, wherein the measuring movement comprises measuring inertial information via one or more inertial sensors placed on the body, and wherein the EMG signals and inertial information are measured simultaneously.

8. The method of claim 1, wherein the plurality of electrodes are sized to cover at least a portion of a plurality of muscles on each of the opposite symmetrical limbs.

9. The method of claim 1, wherein a total number of movements of the symmetrical limbs are determined from a number of contractions of the active muscles of the symmetrical limbs during the exercise.

10. The method of claim 1, wherein the exercise is one requiring a same rhythm and movement of the opposite symmetrical limbs.

11. The method of claim 1, wherein the opposite symmetrical limbs further comprise arms of the individual.

12. The method of claim 1, wherein the measuring EMG signals comprises simultaneously measuring EMG signals from the at least one measuring electrode and the at least one grounding electrode on each of the opposite symmetrical limbs.

13. The method of claim 1, wherein the outfit comprises trunks or trousers that cover at least a portion of each leg of the individual, and wherein the at least one measuring electrode and at least one grounding electrode for each opposite symmetrical limb are located proximate the respective leg extending through the trunks or trousers.

14. The method of claim 1, wherein the transmitting is done wirelessly from the first computing device to the second device.

15. A method for monitoring exercise performance in an individual comprising:
   measuring electromyogram (EMG) signals from one or more active muscles during an exercise by an individual via a plurality of electrodes and at least one grounding electrode, wherein the plurality of electrodes comprise at least one electrode on each of opposite symmetrical limbs of the individual, and wherein the plurality of electrodes and at least one grounding electrode are associated with an outfit during the exercise;
   measuring movement of the individual during the exercise via one or more sensors associated with the individual;
   determining, with a first computing device, results of the exercise from both the measured EMG signals and the measured movement, and
   transmitting the results from the first computing device to at least a second device;
   wherein the exercise comprises a running activity, and
   wherein the results are calculated from the running activity based upon measuring EMG signals from electrodes on a front side of a thigh which indicate damping by a presence of a foot of the individual being on the ground and upon measuring EMG signals from electrodes on a back side of the thigh which indicate a lifting off movement of the foot.

16. The method of claim 15, wherein the measuring movement comprises measuring an inertia of the individual during the running activity via one or more inertial sensors, and wherein a duration of time of the foot being on the ground for each step of the running activity for each leg is determined by measuring a duration between a starting point, wherein EMG signals indicate initial activation of muscles on the front side of the thigh, and an ending point, wherein the plurality of inertial sensors indicate a minimum of vertical acceleration.

17. The method of claim 16, wherein the results of the running activity comprise one or more of a proceeding velocity, a pace length, and a pace rhythm.

* * * * *